(12) United States Patent
Dusseljee et al.

(10) Patent No.: US 11,484,403 B2
(45) Date of Patent: Nov. 1, 2022

(54) INJECTOR FOR INTRODUCING A CAPSULAR TENSION RING, AND ASSEMBLY AND METHOD FOR SUCH AN INJECTOR

(71) Applicant: OPHTEC B.V., Groningen (NL)

(72) Inventors: Jan Hendrik Dusseljee, Peize (NL); Roelof Speelman, Peize (NL); Alfred Willem Wassenburg, Assen (NL)

(73) Assignee: OPHTEC B.V., Groningen (NL)

( * ) Notice: Subject to any disclaimer, the term of this patent is extended or adjusted under 35 U.S.C. 154(b) by 283 days.

(21) Appl. No.: 16/762,219

(22) PCT Filed: Nov. 2, 2018

(86) PCT No.: PCT/NL2018/050736
§ 371 (c)(1),
(2) Date: May 7, 2020

(87) PCT Pub. No.: WO2019/098822
PCT Pub. Date: May 23, 2019

(65) Prior Publication Data
US 2020/0345480 A1 Nov. 5, 2020

(30) Foreign Application Priority Data

Nov. 16, 2017 (NL) ...................... 2019922

(51) Int. Cl.
*A61F 2/16* (2006.01)

(52) U.S. Cl.
CPC ............ *A61F 2/167* (2013.01); *A61F 2/1694* (2013.01); *A61F 2240/001* (2013.01); *A61F 2250/009* (2013.01)

(58) Field of Classification Search
CPC .. A61F 2/167; A61F 2/1694; A61F 2240/001; A61F 2250/009
See application file for complete search history.

(56) References Cited

U.S. PATENT DOCUMENTS

| 5,242,449 A | 9/1993 | Zaleski |
| 5,807,400 A | 9/1998 | Chambers et al. |
| (Continued) | | |

FOREIGN PATENT DOCUMENTS

WO    WO-2005097240 A1 * 10/2005    ........ A61M 5/31555

OTHER PUBLICATIONS

International Search Report and Written Opinion for the International Patent Application No. PCT/NL2018/050736, dated Feb. 14, 2019, 9 pages.

*Primary Examiner* — Paul B Prebilic
(74) *Attorney, Agent, or Firm* — KDB Firm PLLC

(57) ABSTRACT

An injector for introducing a capsular tension ring and intended for once-only use, and a method for manufacturing such an injector. The injector includes: a housing extending in longitudinal direction of the injector, and a throughfeed channel. A plunger is arranged movably in the channel and includes an engaging means for engaging the capsular tension ring, and further includes a guide element on a guide arm. A spring mechanism co-acts with the plunger and is configured to displace the plunger from a starting state, in which the engaging means engages the capsular tension ring, to an activating state in which the capsular tension ring is carried inward into the throughfeed channel. The housing has a guide with first and second channel parts, and a wall part for carrying the guide element from the first to the second channel part, and the first channel part is provided with a resistance threshold.

20 Claims, 5 Drawing Sheets

(56) References Cited

U.S. PATENT DOCUMENTS

| | | |
|---|---|---|
| 6,749,631 B1 | 6/2004 | Pietrini et al. |
| 10,751,168 B2 * | 8/2020 | Midorikawa .......... A61F 2/1667 |
| 2009/0143810 A1 * | 6/2009 | Kitamura ........... A61B 5/15117 |
| | | 606/181 |
| 2015/0133946 A1 * | 5/2015 | Horvath .............. A61F 9/00781 |
| | | 606/108 |
| 2017/0172798 A1 | 6/2017 | Horvath et al. |

* cited by examiner

INJECTOR FOR INTRODUCING A CAPSULAR TENSION RING, AND ASSEMBLY AND METHOD FOR SUCH AN INJECTOR

This is a national stage application filed under 35 U.S.C. § 371 of pending international application PCT/NL2018/050736, filed Nov. 2, 2018, which claims priority to Netherlands Patent application NL 2019922, filed Nov. 16, 2017, the entirety of which applications are hereby incorporated by reference herein.

The invention relates to an injector with which it is possible to introduce a capsular tension ring, also referred to as CTR, into an eye. Such a tension ring has been developed so as to be introduced using the injector for the purpose of stabilizing the so-called capsular bag. This is applied for instance in case of a so-called zonular rupture which can possibly cause a displacement of a lens in an eye. The injector according to the invention is specifically intended for once-only use in respect of, among others, hygienic guidelines.

A reusable metal injector is known in practice. A new tension ring always had to be placed here by the user in or on the injector. This requires operations which must be performed by this user. This entails additional requirements in respect of cleaning and sterilization.

Another injector known in practice is intended for once-only use and makes use of a mechanism in which the tension ring is as it were pulled into the interior of the injector by sliding a hook or handgrip rearward. A lock is arranged here on the outer side of the injector in order to prevent an undesired sliding of the hook or handgrip.

In the case of another injector known in practice the injector is supplied with the tension ring in packaged state. In this packaged state the ring is located substantially outside the injector and is already in engagement here with a hook element of the injector. The tension ring hereby remains unloaded in the transporting situation, whereby any possible deformations are prevented. When the tension ring is arranged in the injector use is made of a spring mechanism, wherein a user has to exert some force on the injector. The tension ring is hereby arranged substantially wholly in the injector, after which the injector is positioned at the desired location by the user and the tension ring is introduced.

One of the problems with injectors known in practice is that the tension ring can release prematurely from the injector. This has the consequence that the injector is unusable or that the tension ring has to be arranged again by a user, if this is at least still possible. This latter has consequences in respect of cleaning and sterilization.

The present invention has for its object to obviate or at least reduce the above stated problems and thereby provide an injector usable in practice wherein premature release of the tension ring is avoided or at least countered.

This object is achieved with the injector for introducing a capsular tension ring and intended for once-only use, the injector according to the invention comprising:
- a housing provided from a first and a second housing part extending in longitudinal direction of the injector, and a throughfeed channel;
- a plunger arranged substantially movably in the throughfeed channel of the housing and provided with an engaging means configured to engage on the capsular tension ring to be introduced, and further provided with a guide element arranged on a guide arm;
- a spring mechanism which co-acts with the plunger and which is configured to displace the plunger from a starting state, in which the engaging means engages on the capsular tension ring, to an activating state in which the capsular tension ring is carried inward substantially into the throughfeed channel of the injector,
  wherein the housing is provided with a guide configured to at least partially receive the guide element such that the plunger is guidable from the starting state to the activating state,
wherein the guide is provided with a first channel part which substantially extends parallel to the throughfeed channel for guiding the plunger in a forward direction, a second channel part configured to carry the guide element therein at an angle to the throughfeed channel in an at least partially rearward direction such that the spring mechanism can carry the plunger to the activating state, and a wall part for carrying the guide element from the first to the second channel part, wherein the first channel part is provided with a resistance threshold with a resistance height which is smaller than the height of the guide arm.

The injector according to the invention is provided with a housing, wherein a throughfeed channel is provided in the interior of the housing parts. A plunger is provided slidably here in this throughfeed channel. A tension ring can hereby be as it were pulled into the interior of the injector by moving the plunger. Use is made here of a spring mechanism which, after release of the plunger by the user, moves the plunger rearward from the starting state, also designated as the packaging state, to the activating state, also designated as loaded state. During the movement of the plunger the tension ring is as it were pulled into the throughfeed channel. By subsequently moving the activated injector to the desired placing location a user can arrange the tension ring at the desired location in simple manner by pushing back the plunger. The tension ring in packaged state is preferably in engagement with an engaging element, for instance in the form of a hook-shaped element on the engaging means, such that the tension ring can thereby be carried from the starting state to the activating state without the intervention of the user.

According to the invention the injector is further provided with a guide configured to at least partially receive the guide element arranged on a guide arm of the plunger. The guide ensures that the plunger is guidable from the starting state to the activating state. This is made possible by providing a first channel part which runs substantially parallel to the throughfeed channel. If it is desired to activate the injector, a user can move the plunger forward to some extent, wherein the guide element moves in or along the first channel part in a forward direction. The movement the user makes therefore consists of pressing in or moving forward the plunger to some extent which is subsequently moved rearward again by a spring mechanism. This has some similarities to a ballpoint pen principle.

By transferring the guide element from the first channel part to the second channel part the guide element, and thereby the plunger, is stopped in the forward movement. With the subsequent release of the plunger by the user the plunger is then moved rearward by the spring mechanism, wherein the guide element is preferably carried from the second channel part into the throughfeed channel such that it can be moved substantially freely rearward. During this rearward movement the tension ring is carried into the interior of the injector, in particular into the throughfeed channel thereof. The second channel part is provided here at an angle to the throughfeed channel in an at least partially rearward direction so that the guide element can be introduced in effective and gradual manner therein. This makes "loading" of the injector possible in effective manner.

According to the invention the first channel part is also provided with a resistance threshold with a resistance height which is smaller than the height of the guide arm. Providing a resistance threshold in the first channel part achieves that some resistance has to be overcome by the user when displacing the plunger from the starting state such that the user cannot activate the injector by accident. Making the resistance height of the resistance threshold smaller than the height of the guide arm at or on which the guide element is arranged achieves that the resistance is relatively small compared to, among other factors, the stiffness of the guide arm.

The resistance resulting from the resistance height is preferably lower than the resistance provided by the wall part arranged close to the transition from the first to the second channel part. More particularly achieved because the height of this wall part is greater than the resistance height of the resistance threshold is that overshooting of the guide element due to the exertion of too much pressure by a user is avoided. This overshooting does after all have the result that the engaging means of the plunger can come to lie outside the throughfeed channel and the tension ring is released prematurely and at a wrong location. This is avoided by providing two clearly differing resistances, brought about by respectively the resistance height and the wall height, so that a user encounters a relatively limited resistance in order to prevent an undesired activation of the injector and encounters significant resistance in order to ensure that the plunger does not start premature and undesired release of the tension ring.

Tests have shown that the undesired release caused by a user accidentally exerting too much pressure on the plunger is substantially wholly prevented. The effectiveness of the injector according to the invention during use is hereby considerably increased. Also avoided is a user being tempted to nevertheless activate the injector using manual operations on the tension ring in the case of a premature release, whereby cleaning and sterilization can cause problems.

The ratio of the height of the guide arm and the resistance height is preferably greater than 1.5 and preferably even greater than 1.75. Said tests have shown that this ratio results in a sufficient resistance to an undesired activation of the injector.

In addition, a significant distinction is hereby made between the resistance height of the resistance threshold and the height of the wall of the wall part close to the transition from the first to the second channel part. Undesired release of the tension ring is in particular avoided with this combination. In a currently preferred embodiment the resistance height amounts to a maximum of 0.75 mm, and most preferably to a maximum of 0.7 mm. It is found that an easily manageable injector can hereby be realized which is reliable in use. In such a currently preferred embodiment the height of the wall of the wall part is preferably greater than 1.25 mm so that sufficient resistance is thereby provided to a user exerting too much pressure on the plunger. The ratio of the wall height and the resistance height is hereby preferably greater than 1.65. This results in a good balance between the resistance to undesired activation and resistance to undesired exertion of too much pressure.

In an advantageous embodiment according to the invention the guide arm is provided with a length-height ratio of at least 0.05, and preferably at least 0.055.

An effective and easily manageable injector is brought about by providing a minimum length-height ratio. The length is measured here from the start of the arm from the plunger to the centre of the guide element. By providing the guide element on an arm some flexibility is provided to the guide element in transverse direction of the arm. This is desired in the preferred embodiment because the guide element can thereby be carried into a first channel part and subsequently carried via a second channel part to the throughfeed channel, and can move here together with the plunger. Said ratio has been found to be particularly advantageous for also providing sufficient stiffness in addition to sufficient flexibility and freedom of movement of the guide element. This contributes toward further reduction of the risk of the plunger overshooting when the injector is moved from the starting state to the activating state.

In an advantageous embodiment according to the invention a front contact surface of the guide element forms an angle of at least 100° with the longitudinal direction of the guide arm.

Providing an angle for the front surface of the guide element achieves on the one hand that the guide element can surmount thresholds and differences in height between channel parts and throughfeed channel in effective manner while on the other hand maintaining sufficient resistance in the case of a wall part or resistance element.

In a further advantageous embodiment according to the invention the plunger is manufactured from a material comprising a component with a lubricating effect relative to the housing.

The housing is for instance provided from a moulded poly(methyl methacrylate) (PMMA). By providing the plunger with a lubricant, or at least a component with lubricating effect, the plunger will move more easily relative to the housing. Undesired resistance as a result of so-called stick-slip is hereby avoided or at least reduced. This makes transition of the injector from the starting state to the activating state simpler, as well as subsequent release of the tension ring from the activating state. The risk of undesired damage to for instance the eye or parts thereof is hereby avoided.

In a further advantageous embodiment according to the invention the housing is also provided with an end, wherein the end is provided with a chamfering.

Providing an end provided with a chamfering makes it easier for a user to introduce the injector at the desired location in an eye. The risk of damage is significantly reduced by the chamfering. The chamfering is preferably formed by an angle of inclination in the range of 30°-60°, preferably in the range of 40°-50°. Such an angle of inclination has been found to achieve relatively easy introduction of the injector, wherein the risk of damage is minimized.

The invention also relates to an assembly of an injector in the embodiment as described above and a capsular tension ring.

The same advantages and effects apply to such an assembly as described for the injector. Such an assembly is particularly advantageous in supplying the user with a sterile product which is ready for use. Such an assembly is for instance supplied to a user in packaged state. This makes working with an injector in sterile condition easier.

The invention also relates to a method for manufacturing an injector for introducing a capsular tension ring and intended for once-only use, the method comprising of providing an injector in an embodiment as described above.

The method provides similar effects and advantages as described for the injector and/or the assembly. The injector is preferably provided from two housing parts which are produced in a mould, a plunger, a spring mechanism and an end. The housing is made according to a preferred embodiment from a moulded poly(methyl acrylate) (PMMA). It will be apparent that other similar materials are also possible.

The method preferably also comprises the step of attaching a tension ring in the starting state to an engaging element of the engaging means before packaging the assembly. The injector with tension ring can in this way be transferred in sterile manner at a desired moment and at a desired location by a user from the starting state, as in the packaging, to the activating state, wherein the injector is ready for the user.

Further advantages, features and details of the invention will be elucidated on the basis of preferred embodiments thereof, wherein reference is made to the accompanying drawings, in which:

FIG. 1 shows an injector in a possible embodiment according to the invention;

FIG. 2 A-E show views of a housing part of the injector of FIG. 1;

Figure 1:
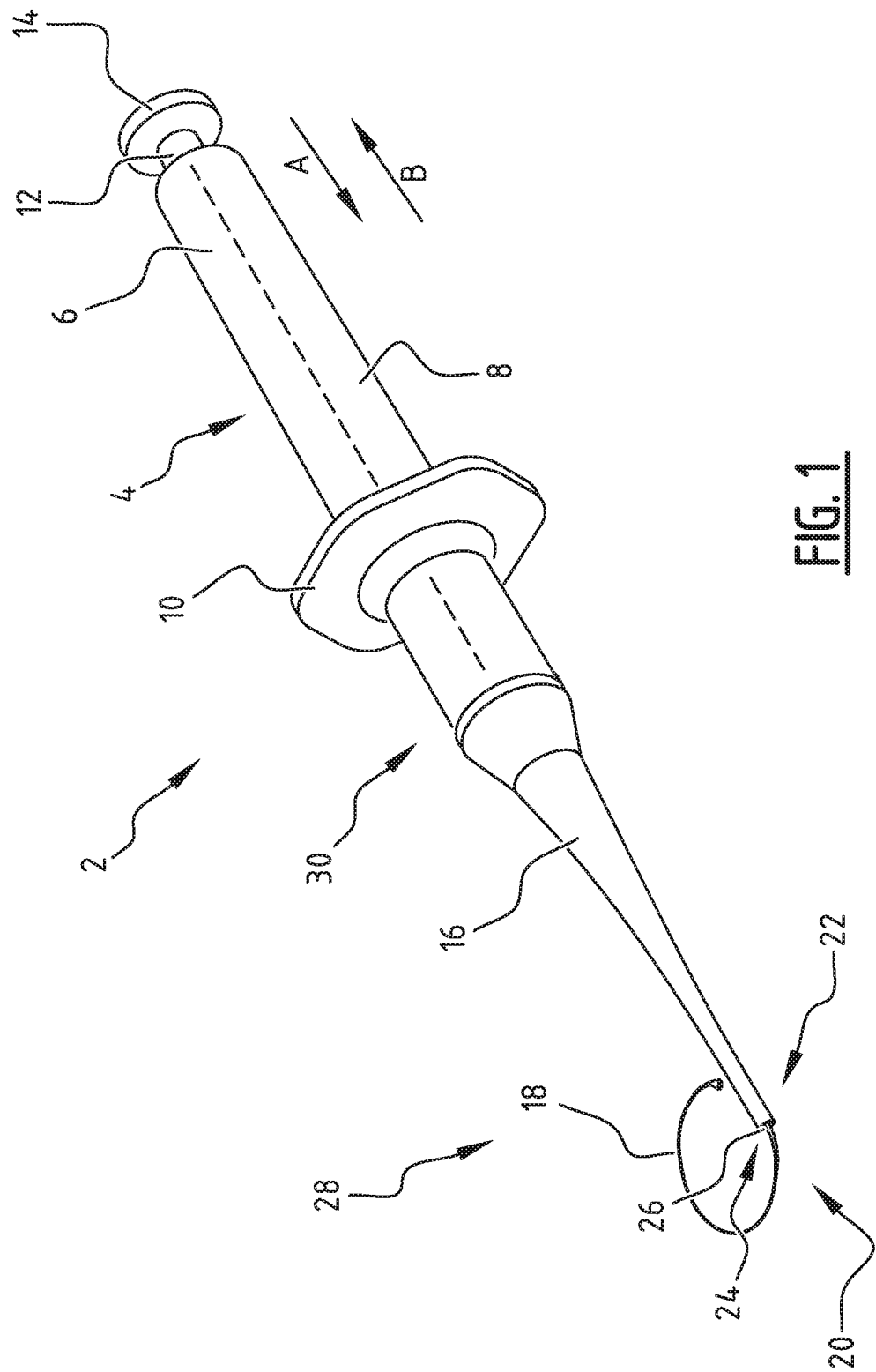

Injector 2 (FIG. 1) is provided with housing 4. In the shown embodiment housing 4 is constructed from first housing part 6 and second housing part 8, wherein a flange or handgrip 10 is provided. Provided in housing 4 is movable plunger 12 which can be moved using handgrip or press button 14. Outlet 16 is provided on the other side of injector 2. In the shown embodiment tension ring 18 with end 20 is provided in outlet 16. For this purpose outlet 16 is provided at outer end 22 thereof with opening 24. In the shown embodiment chamfering 26 is provided here at an angle of about 45°. Assembly 28 is formed in the shown embodiment by the combination of injector 2 with tension ring 18.

Assembly 28 is preferably packaged and supplied to the user in sterile state. After unpacking injector 2 and before placing tension ring 18 in an eye by a user, handgrip 14 of plunger 12 is pressed in to some extent in direction A and subsequently pressed rearward in direction B by spring mechanism 30, wherein tension ring 18 is carried into the interior of injector 2. When a user then presses in handgrip 14 again, plunger 12 moves forward again in direction A, wherein ring 18 can be released at the desired position.

Figure 2A:
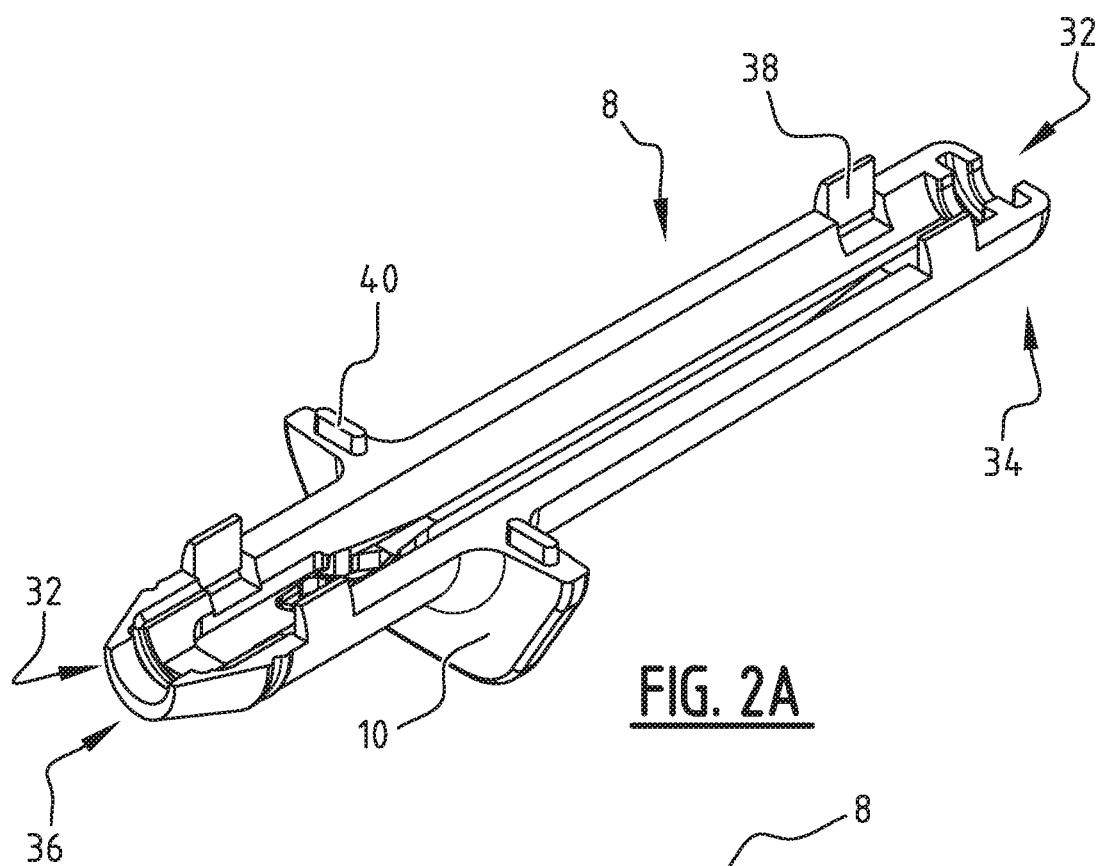
Figure 2B:
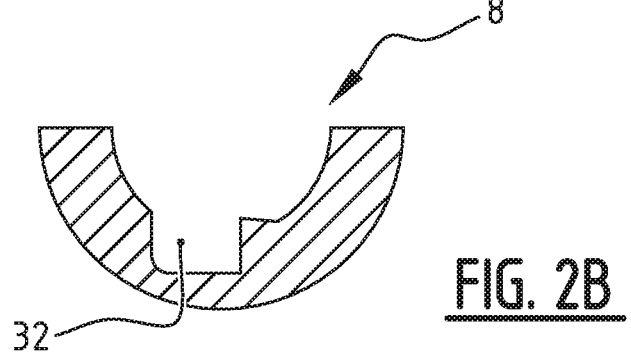
Figure 2C:
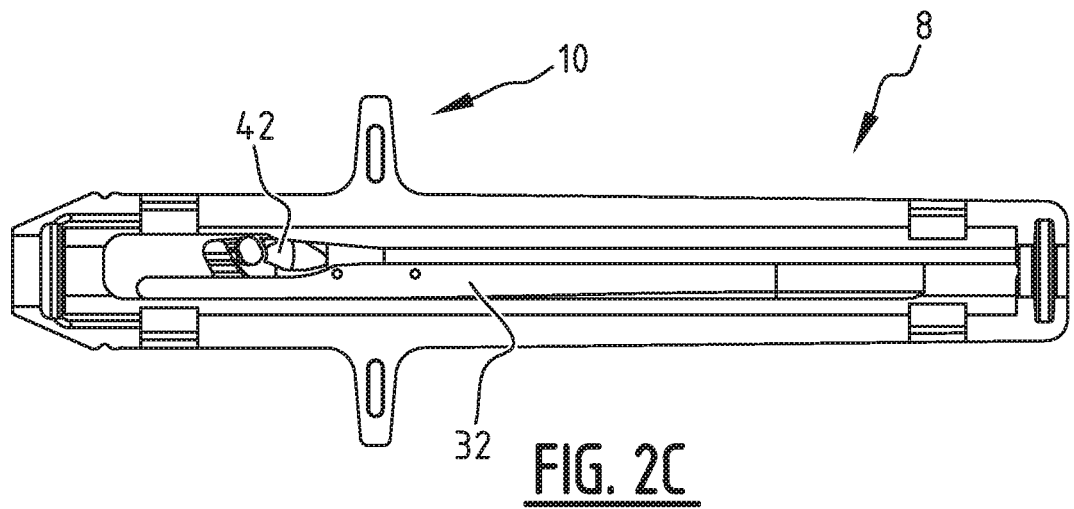

Lower housing part 8 (FIG. 2A-C) is provided with throughfeed channel 32 which extends substantially parallel to the longitudinal direction of housing part 8 from rear end 34 to front end 36. In the shown embodiment housing part 8 is provided with a number of clamping protrusions 38 which co-act with corresponding parts on the other housing part 6 such that housing parts 6, 8 can be brought together. Use is preferably made of positioning lugs 40 which fit into corresponding recesses of the other housing part 6 so as to thereby increase the stability of the assembled housing 44. Guide 42 is further provided in housing part 8 (FIG. 2C).

Figure 2D:
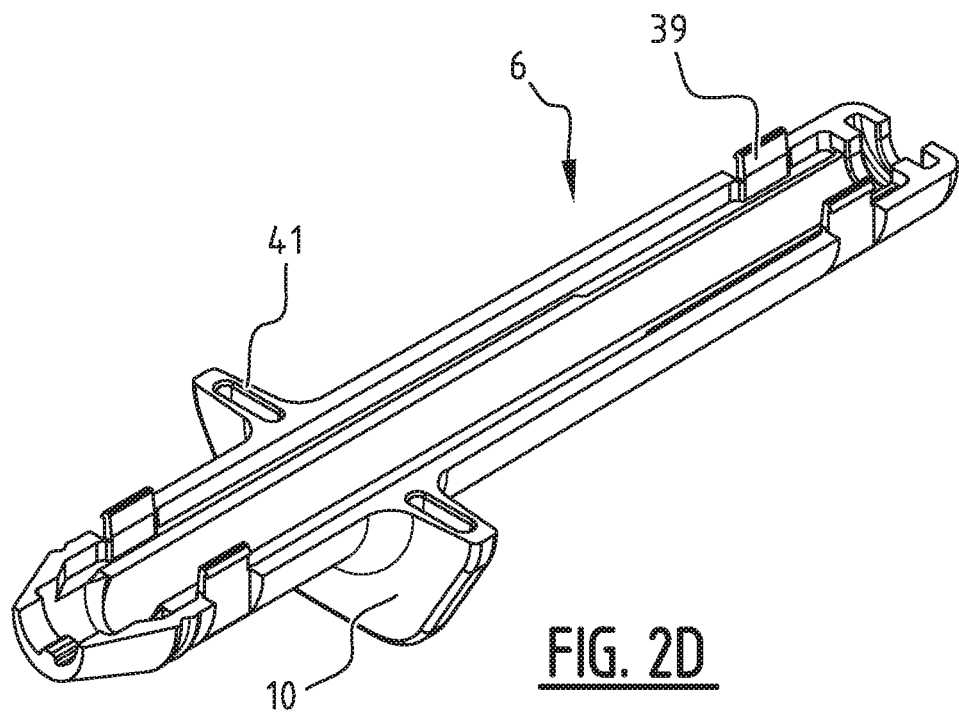

Housing part 6 (FIG. 2D) is provided with said corresponding clamping protrusions 39. In the shown embodiment housing part 6 is also provided with recesses 41.

Figure 2E:
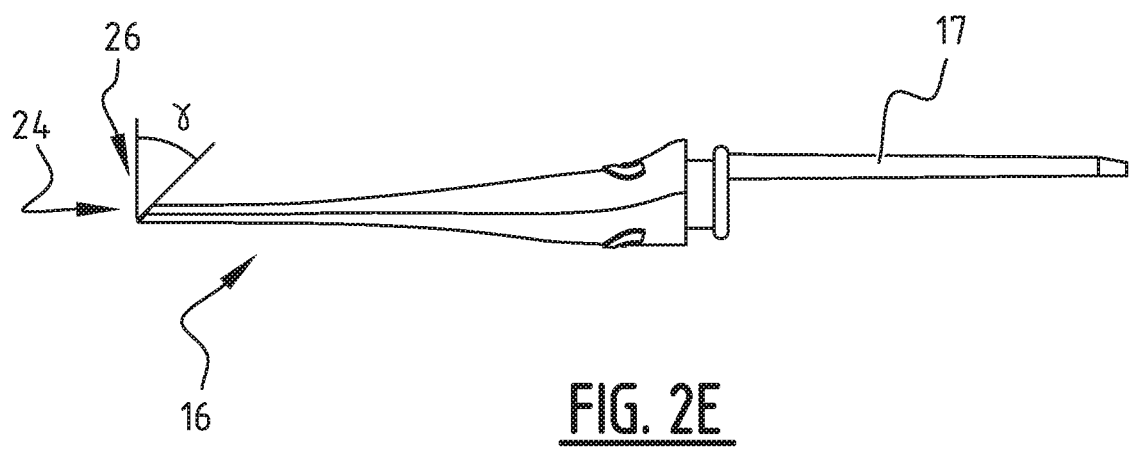

Outlet 16 (FIG. 2E) has chamfering 26 with angle γ, as well as orienting element 17.

Figure 3:
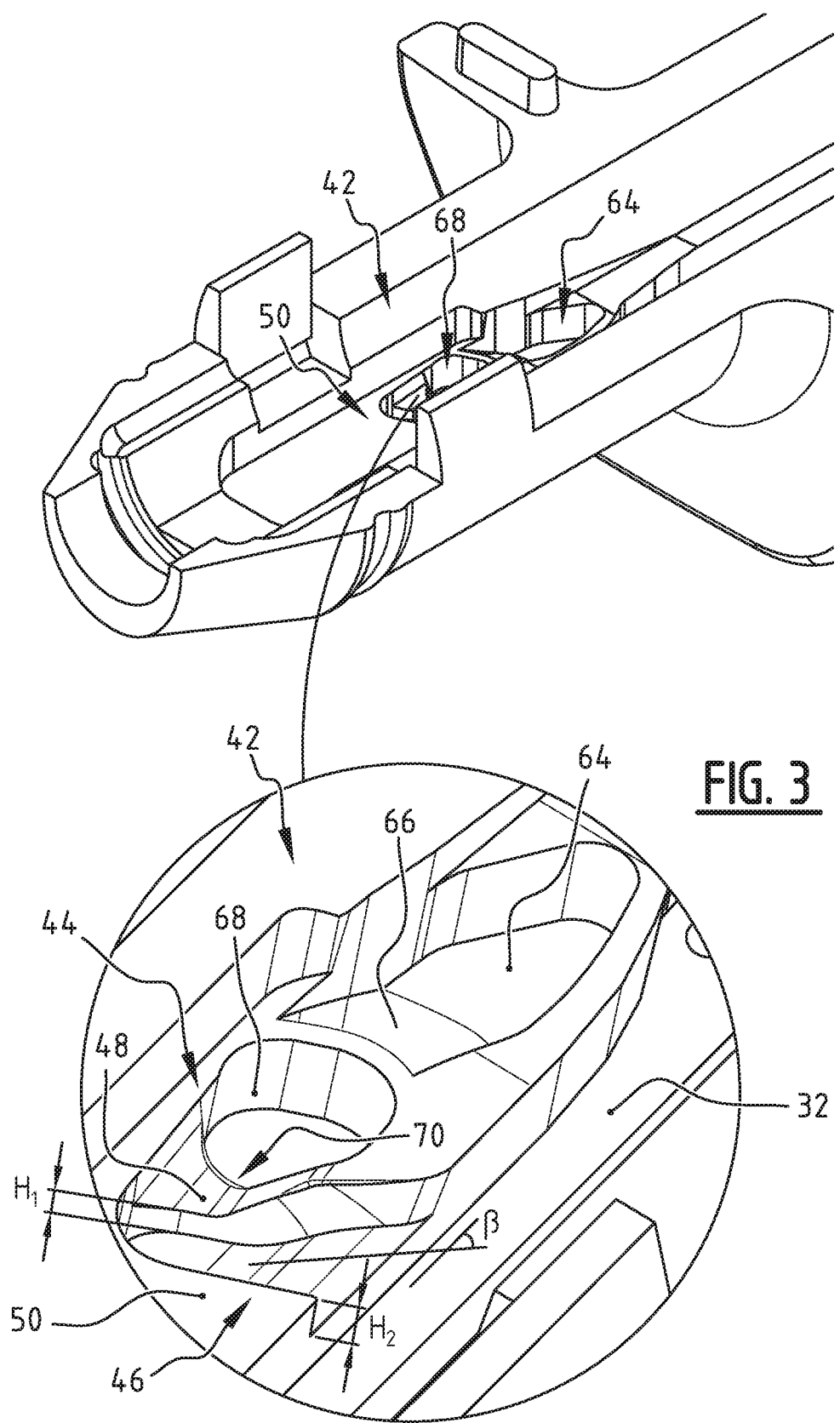
FIG. 3 is a view of a detail of the guide of FIG. 2.

Guide 42 (FIG. 3) comprises first channel part 44 extending substantially parallel to throughfeed channel 32 and second channel part 46 extending at an angle β to throughfeed channel 32. In the shown embodiment resistance element 48 is provided as a threshold with height $H_1$. Wall part 50 with height $H_2$ forms the transition between first channel part 44 and second channel part 46.

Figure 4A:
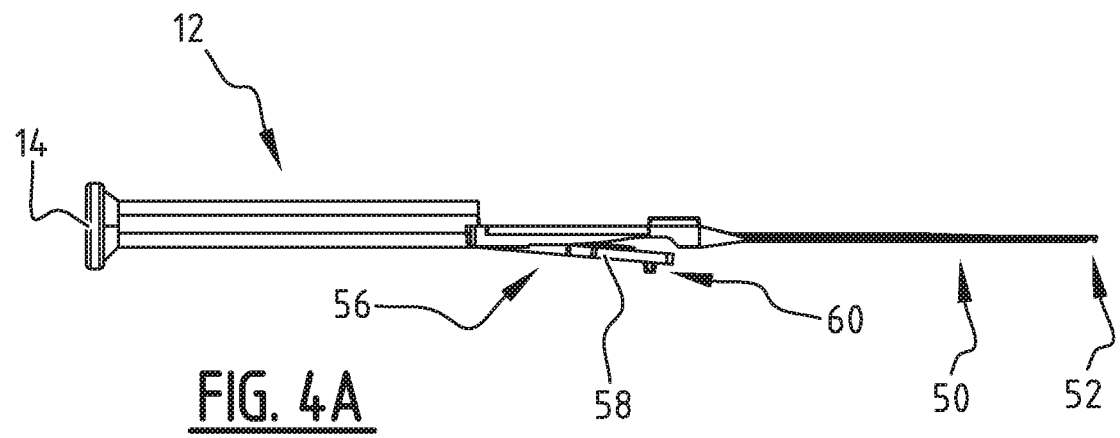
FIG. 4A is a side view of the plunger of the injector of FIG. 1.
Figure 4B:
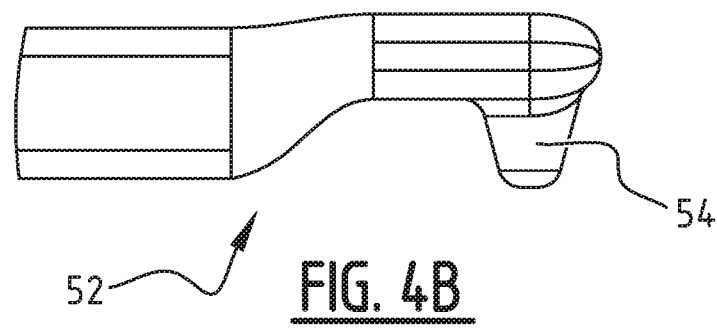
FIG. 4B is a detail view of a hook part of the plunger.
Figure 4C:
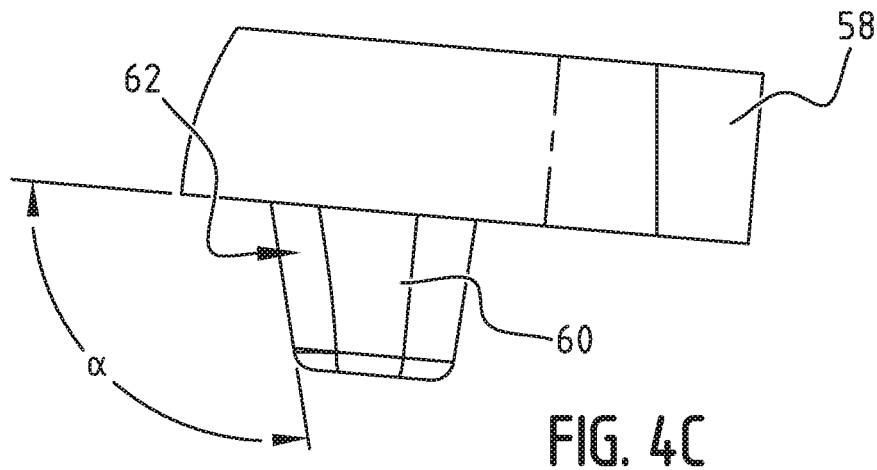
FIG. 4C is a detail view of a guide element of the plunger.

Plunger 12 with press button or handgrip 14 (FIG. 4A) is provided with outer end 50 with hook part 52 (FIG. 4B). Engaging element 52 is provided with hook 54. Plunger 12 is further provided with guide 56 with arm 58 and guide element 60. Guide element 60 (FIG. 4C) is provided with front contact surface 62 which is at an angle α of about 104° relative to the longitudinal direction of arm 58.

In the shown embodiment guide element 60 is carried during mounting via chamber 64 and transition 66 into chamber 68 (FIG. 3) which forms part of first channel part 44. Guide element 60 is pressed over threshold 48 by pressing in plunger 12. Threshold 48 is preferably provided with transition 70. Plunger 12 can subsequently be pressed further in direction A until it comes up against wall part 50. A further movement of plunger 12 in direction A is blocked by adapting heights $H_1$ of resistance element 48 and $H_2$ of wall part 50. As a result of press button 14 being released by the user plunger 12 is moved rearward in direction B via spring mechanism 30. Guide element 60 is carried here to throughfeed channel 32 at angle β via second channel part 46. Once arrived in throughfeed channel 32 plunger 12 moves further rearward in direction B, wherein tension ring 18 is substantially wholly received in injector 2. If after positioning of injector 2 plunger 12 is pressed in again by a user via press button 14, plunger 12 will once again be moved forward in direction A and, unimpeded by wall part 50, can be fed through further such that hook 54 of engaging means 52 eventually protrudes from opening 24 of outlet 16. Tension ring 18 with ring end 20 is hereby released and is thereby placeable at a desired position.

The present invention is by no means limited to the above described preferred embodiments thereof. The rights sought are defined by the following claims, within the scope of which many modifications can be envisaged.

The invention claimed is:

1. An injector for introducing a capsular tension ring and intended for once-only use, the injector comprising:

a housing provided from a first and a second housing part extending in longitudinal direction of the injector, and a throughfeed channel;

a plunger arranged movably in the throughfeed channel of the housing and provided with an engaging means configured to engage on the capsular tension ring to be introduced, and further provided with a guide element arranged on a guide arm; and a spring mechanism which co-acts with the plunger and which is configured to displace the plunger from a starting state, in which the engaging means engages on the capsular tension ring, to an activating state in which the capsular tension ring is carried inward into the throughfeed channel of the injector, wherein the housing is further provided with a guide configured to at least partially receive the guide element such that the plunger is guidable from the starting state to the activating state, wherein the guide is provided with a first channel part which extends parallel to the throughfeed channel for guiding the plunger in a forward direction, a second channel part configured to carry the guide element therein at an angle to the throughfeed channel in an at least partially rearward direction such that the spring mechanism can carry the plunger to the activating state, and a wall part for carrying the guide element from the first to the second channel part, and wherein the first channel part is provided with a resistance threshold with a resistance height which is smaller than the height of the guide arm.

2. The injector as claimed in claim 1, wherein the ratio of the height of the guide arm and the resistance height is greater than 1.5.

3. The injector as claimed in claim 1, wherein the resistance height amounts to a maximum of 0.75 mm.

4. The injector as claimed in claim 1, wherein the wall part is provided with a wall height greater than 1.25 mm.

5. The injector as claimed in claim 1, wherein the guide arm is provided with a length-height ratio of at least 0.05.

6. The injector as claimed in claim 1, wherein a front contact surface of the guide element makes an angle of at least 100° with the longitudinal direction of the guide arm.

7. The injector as claimed in claim 1, wherein the plunger is manufactured from a material comprising a component with a lubricating effect relative to the housing.

8. The injector as claimed in claim 1, wherein the housing is further provided with an end, wherein the end is provided with a chamfering.

9. The injector as claimed in claim 8, wherein the chamfering comprises an angle of inclination in the range of 30°-60°.

10. An assembly of an injector and a capsular tension ring, wherein the injector for introducing a capsular tension ring and intended for once-only use comprises:
   a housing provided from a first and a second housing part extending in longitudinal direction of the injector, and a throughfeed channel;
   a plunger arranged movably in the throughfeed channel of the housing and provided with an engaging means configured to engage on the capsular tension ring to be introduced, and further provided with a guide element arranged on a guide arm; and
   a spring mechanism which co-acts with the plunger and which is configured to displace the plunger from a starting state, in which the engaging means engages on the capsular tension ring, to an activating state in which the capsular tension ring is carried inward into the throughfeed channel of the injector,
   wherein the housing is further provided with a guide configured to at least partially receive the guide element such that the plunger is guidable from the starting state to the activating state,
   wherein the guide is provided with a first channel part which extends parallel to the throughfeed channel for guiding the plunger in a forward direction, a second channel part configured to carry the guide element therein at an angle to the throughfeed channel in an at least partially rearward direction such that the spring mechanism can carry the plunger to the activating state, and a wall part for carrying the guide element from the first to the second channel part, and
   wherein the first channel part is provided with a resistance threshold with a resistance height which is smaller than the height of the guide arm.

11. A method for manufacturing an injector for introducing a capsular tension ring and intended for once-only use, the method comprising providing an injector for introducing a capsular tension ring and intended for once-only use, the injector comprising:
   a housing provided from a first and a second housing part extending in longitudinal direction of the injector, and a throughfeed channel;
   a plunger arranged movably in the throughfeed channel of the housing and provided with an engaging means configured to engage on the capsular tension ring to be introduced, and further provided with a guide element arranged on a guide arm; and
   a spring mechanism which co-acts with the plunger and which is configured to displace the plunger from a starting state, in which the engaging means engages on the capsular tension ring, to an activating state in which the capsular tension ring is carried inward into the throughfeed channel of the injector,
   wherein the housing is further provided with a guide configured to at least partially receive the guide element such that the plunger is guidable from the starting state to the activating state,
   wherein the guide is provided with a first channel part which extends parallel to the throughfeed channel for guiding the plunger in a forward direction, a second channel part configured to carry the guide element therein at an angle to the throughfeed channel in an at least partially rearward direction such that the spring mechanism can carry the plunger to the activating state, and a wall part for carrying the guide element from the first to the second channel part, and
   wherein the first channel part is provided with a resistance threshold with a resistance height which is smaller than the height of the guide arm.

12. The method as claimed in claim 11, further comprising arranging a capsular tension ring in the starting state.

13. The injector as claimed in claim 1, wherein the ratio of the height of the guide arm and the resistance height is greater than 1.75.

14. The injector as claimed in claim 1, wherein the resistance height amounts to a maximum of 0.7 mm.

15. The injector as claimed in claim 1, wherein the guide arm is provided with a length-height ratio of at least 0.055.

16. The injector as claimed in claim 8, wherein the chamfering comprises an angle of inclination in the range of 40°-50°.

17. The injector as claimed in claim 2, wherein the resistance height amounts to a maximum of 0.75 mm.

18. The injector as claimed in claim 17, wherein the wall part is provided with a wall height greater than 1.25 mm.

19. The injector as claimed in claim 18, wherein the guide arm is provided with a length-height ratio of at least 0.05.

20. The injector as claimed in claim 19, wherein the housing is further provided with an end, wherein the end is provided with a chamfering, and wherein the chamfering comprises an angle of inclination in the range of 30°-60°.

* * * * *